(12) United States Patent
Bohlen et al.

(10) Patent No.: US 11,921,053 B2
(45) Date of Patent: *Mar. 5, 2024

(54) METHODS AND SYSTEMS FOR INCLUSION ANALYSIS

(71) Applicant: FEI Company, Hillsboro, OR (US)

(72) Inventors: Jean-Marc Bohlen, Ecublens (CH); Cornelis van Beek, Pittsburgh, PA (US)

(73) Assignee: FEI Company, Hillsboro, OR (US)

( * ) Notice: Subject to any disclaimer, the term of this patent is extended or adjusted under 35 U.S.C. 154(b) by 182 days.

This patent is subject to a terminal disclaimer.

(21) Appl. No.: 17/496,605

(22) Filed: Oct. 7, 2021

(65) Prior Publication Data

US 2022/0026373 A1 Jan. 27, 2022

Related U.S. Application Data

(63) Continuation of application No. 16/825,835, filed on Mar. 20, 2020, now Pat. No. 11,150,197.

(51) Int. Cl.
| | | |
|---|---|---|
| *G01N 21/892* | (2006.01) | |
| *G01N 21/67* | (2006.01) | |
| *G01N 23/2252* | (2018.01) | |

(52) U.S. Cl.
CPC ........... *G01N 21/892* (2013.01); *G01N 21/67* (2013.01); *G01N 23/2252* (2013.01); *G01N 2021/8925* (2013.01)

(58) Field of Classification Search
CPC ......... G01N 2223/076; G01N 33/2045; G01N 21/67; G01N 2223/071; G01N 2223/624; G01N 2021/8925; G01N 21/892; G01N 2223/079; G01N 2223/645; G01N 23/2252; G01N 21/63; G01N 23/223; G01N 1/125; G01N 21/718; G01N 21/72; G01N 2223/03; G01N 2223/09; G01N 2223/102; G01N 2223/652; G01N 23/04; G01N 23/2206; G01N 23/2251; G01N 33/205; G01N 1/02; G01N 1/12; G01N 1/1409; G01N 1/20; G01N 1/28; G01N 1/286; G01N 1/34; G01N 2001/1031; G01N 2001/2866;

(Continued)

(56) References Cited

U.S. PATENT DOCUMENTS

| | | | | |
|---|---|---|---|---|
| 8,730,470 | B2 * | 5/2014 | McLane | G01N 21/67 356/326 |
| 2013/0015351 | A1 * | 1/2013 | Kooijman | H01J 37/28 250/307 |

(Continued)

FOREIGN PATENT DOCUMENTS

| | | | | |
|---|---|---|---|---|
| EP | 3786626 | A1 * | 3/2021 | ......... G01N 23/2252 |
| JP | 2003098130 | A | * | 4/2003 |

(Continued)

*Primary Examiner* — Michael P Stafira (57) ABSTRACT

Various methods and systems are provided for analyzing sample inclusions. As one example, a correction factor may be generated based on inclusion properties of a first sample determined using both an optical emission spectrometry (OES) system and a charged-particle microscopy with energy dispersive X-ray spectroscopy (CPM/EDX) system. The OES system may be calibrated with the correction factor. The inclusion properties of a second, different, sample may be determined using the calibrated OES system.

16 Claims, 7 Drawing Sheets

(58) Field of Classification Search
CPC ..... G01N 2001/2873; G01N 2021/845; G01N 2021/8455; G01N 2035/00158; G01N 2035/1041; G01N 21/25; G01N 21/3563; G01N 21/65; G01N 21/84; G01N 21/8422; G01N 33/20; G01N 33/202; G01N 33/2022; G01N 35/1011
See application file for complete search history.

(56) References Cited

U.S. PATENT DOCUMENTS

| | | | | |
|---|---|---|---|---|
| 2014/0021346 | A1* | 1/2014 | Stoks | G01N 23/225 |
| | | | | 250/307 |
| 2014/0070095 | A1* | 3/2014 | Schoenmakers | G06T 11/005 |
| | | | | 250/311 |
| 2014/0117231 | A1* | 5/2014 | Owen | H01J 37/28 |
| | | | | 250/307 |
| 2021/0148842 | A1* | 5/2021 | Terborg | G01B 15/025 |

FOREIGN PATENT DOCUMENTS

| | | | | | |
|---|---|---|---|---|---|
| JP | 2014021124 | A | * | 2/2014 | ........... G01N 23/223 |
| KR | 20230069973 | A | * | 5/2023 | |
| WO | WO-2014028488 | A1 | * | 2/2014 | ............ H01J 37/244 |

* cited by examiner

METHODS AND SYSTEMS FOR INCLUSION ANALYSIS

CROSS-REFERENCE TO RELATED APPLICATIONS

This application is an application under 35 U.S.C. § 120 of pending U.S. application Ser. No. 16/825,835, filed Mar. 20, 2020, which application claims the benefit under 35 U.S.C. § 119(e) of U.S. Provisional Application No. 62/824,148, filed Mar. 26, 2019. The entire contents of the aforementioned applications are incorporated by reference herein.

FIELD OF THE INVENTION

The present description relates generally to methods and systems for analyzing inclusions in a sample, and more particularly, to analyzing inclusions using both optical emission spectroscopy and charged-particle microscopy with energy dispersive x-ray spectroscopy.

BACKGROUND OF THE INVENTION

The property and quality of steel are significantly affected by inclusions (such as non-metallic inclusions) formed in the steel during steel production. Monitoring and controlling inclusion properties during the steel production is important to the cost-effective production of high-quality steel and to steel quality. The inclusion property may be determined using the optical emission spectroscopy (OES) or the scanning electron microscopy with energy dispersive X-ray spectroscopy (SEM/EDX).

OES is an analytical technique used to analyze the chemical composition of the sample, in other words, to determine the concentrations of a broad range of elements present in the sample. OES can also be used to evaluate the inclusion content of the sample. During OES analysis, a small portion of the sample may be vaporized by electrical discharge (or spark). The atoms in the vaporized sample are excited and emit light at the element specific emission wavelengths. The type, size, and amount of the inclusions may be determined by analyzing the emission specific to the elements composing the inclusions.

SEM/EDX analysis provides structural and elemental information of the sample. During SEM/EDX analysis, responsive to an electron beam impinging the sample, various radiations, including back-scattered electrons, secondary electrons, and X-rays, may emit from the sample. The back-scattered electrons or the secondary electrons may be used to image the structure of the sample, while the energy distribution of the emitted X-rays may indicate the composition of the sample. By acquiring both the back-scattered and/or secondary electrons and the X-ray emission, SEM/EDX may image the distribution and composition of the sample inclusions.

SUMMARY

In one embodiment, a method for analyzing sample inclusions comprises generating a correction factor based on inclusion properties of a first sample determined using both an optical emission spectrometry (OES) system and a charged-particle microscopy with energy dispersive X-ray spectroscopy (CPM/EDX) system, and determining an inclusion property of a second, different, sample using the OES system calibrated with the correction factor. In this way, the OES system and the CPM/EDX system may be synergized to provide fast and accurate inclusion analysis.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Like reference numerals refer to corresponding parts throughout the several views of the drawings.

DETAILED DESCRIPTION OF EMBODIMENTS

Figure 1:
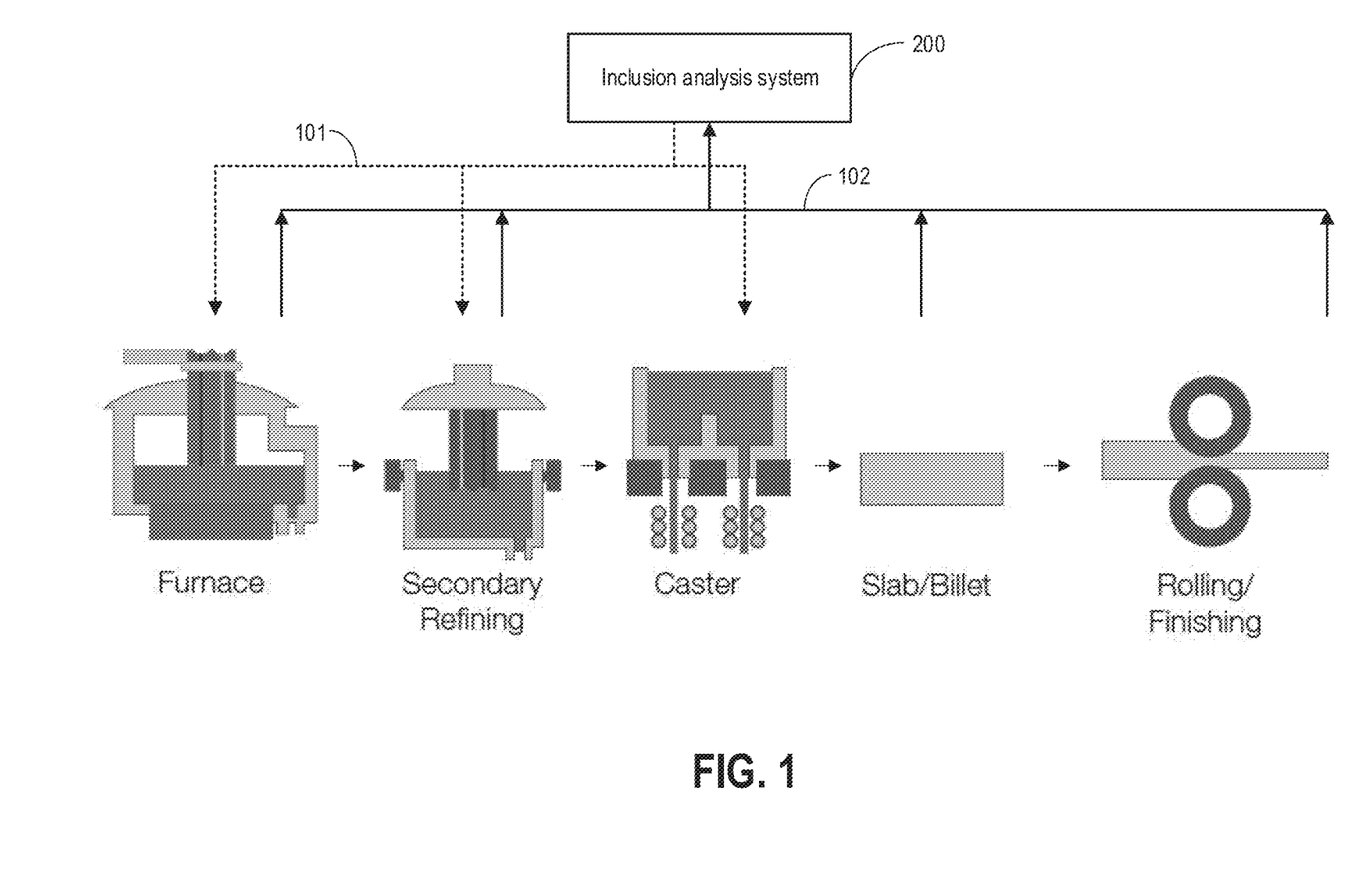
FIG. 1 illustrates inclusion analysis performed at various stages of steel production.

The following description relates to systems and methods for analyzing inclusions in a sample. For example, as shown in FIG. 1, inclusion properties of samples sampled at various stages of steel production may be analyzed with an inclusion analysis system. Based on the inclusion properties, the steel production process may be adjusted to ensure desired inclusion properties in the final steel product.

Both optical emission spectrometry (OES) and charged-particle microscopy with energy dispersive X-ray spectroscopy (CPM/EDX) may be used for analyzing the inclusion property. The OES analyzes a volume of the sample, while the CPM/EDX, such as scanning electron microscopy with energy dispersive X-ray spectroscopy (SEM/EDX), analyzes a surface of the sample. Each analytical method has its advantages and disadvantages. For example, comparing to CPM/EDX, OES requires less time for sample preparation and sample analysis. However, OES analysis is only sensitive to inclusions around 1-15 um in diameter. The CPM/EDX analysis, on the other hand, provides a direct measurement of composition, shape, and size distribution of the inclusion. In steel production, obtaining accurate and timely inclusion property information is critical for in-process inclusion control.

Figure 2:
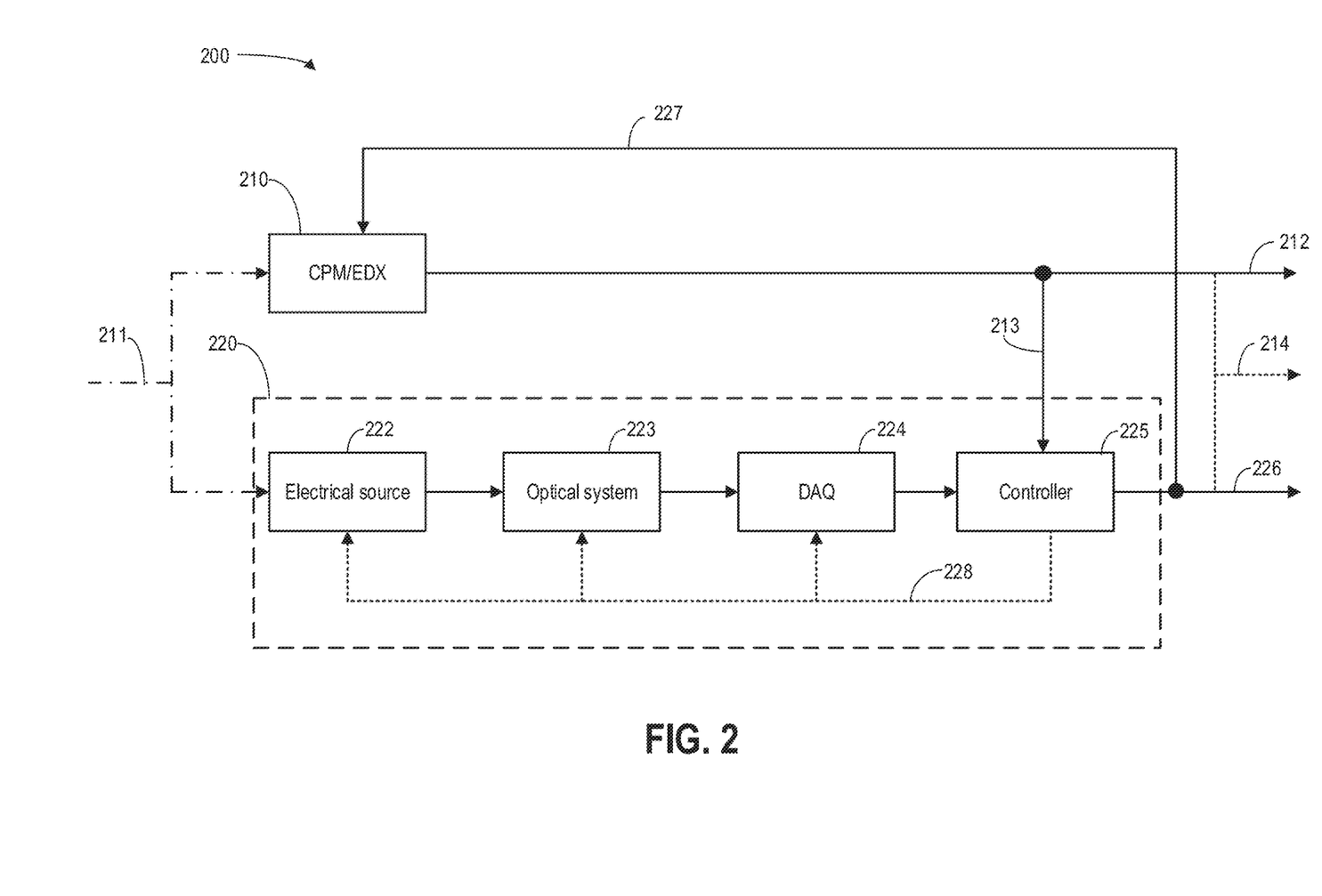
FIG. 2 is a diagram of an inclusion analysis system according to one exemplary embodiment of the invention.
Figure 3:
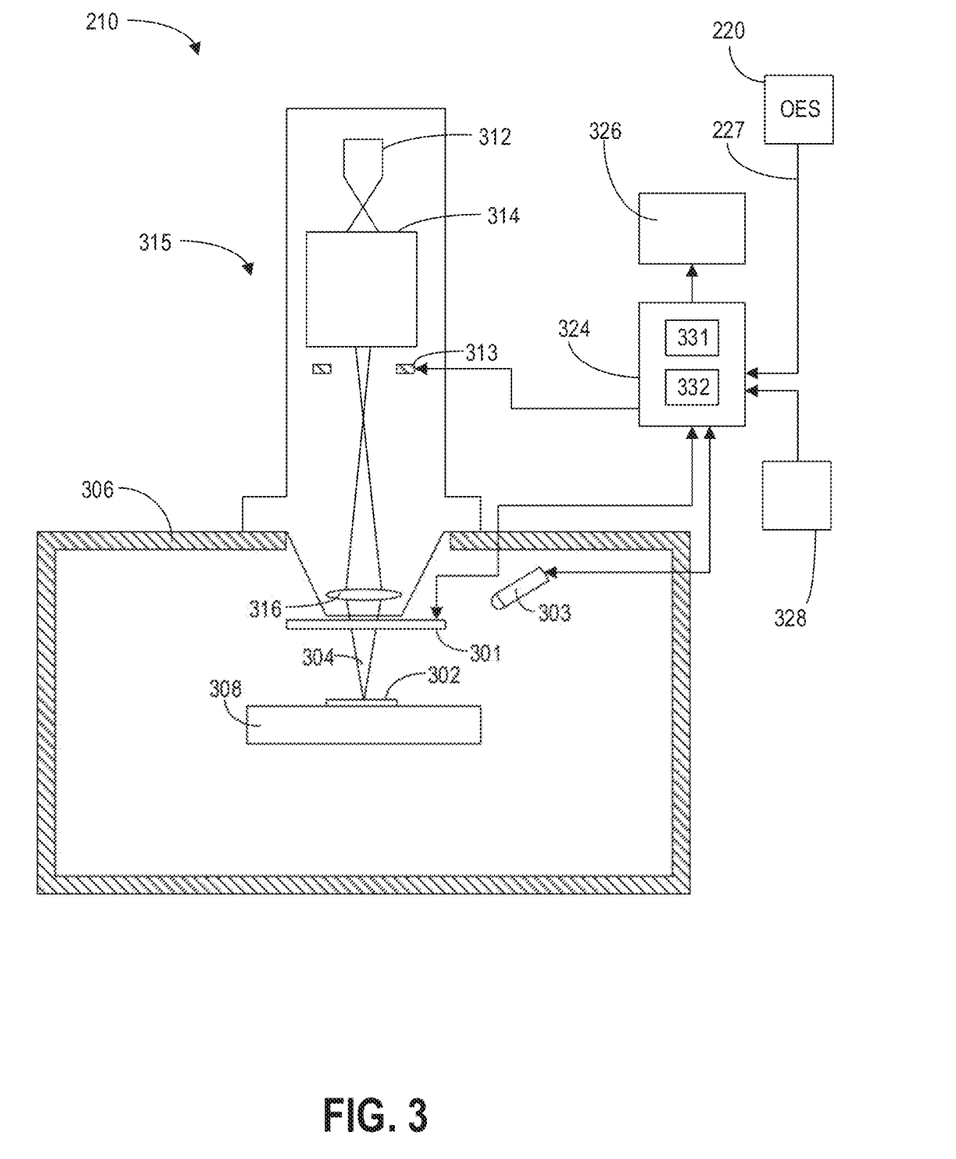
FIG. 3 is a diagram of an example charged-particle microscopy with energy dispersive X-ray spectroscopy (CPM/EDX) system.
Figure 4:
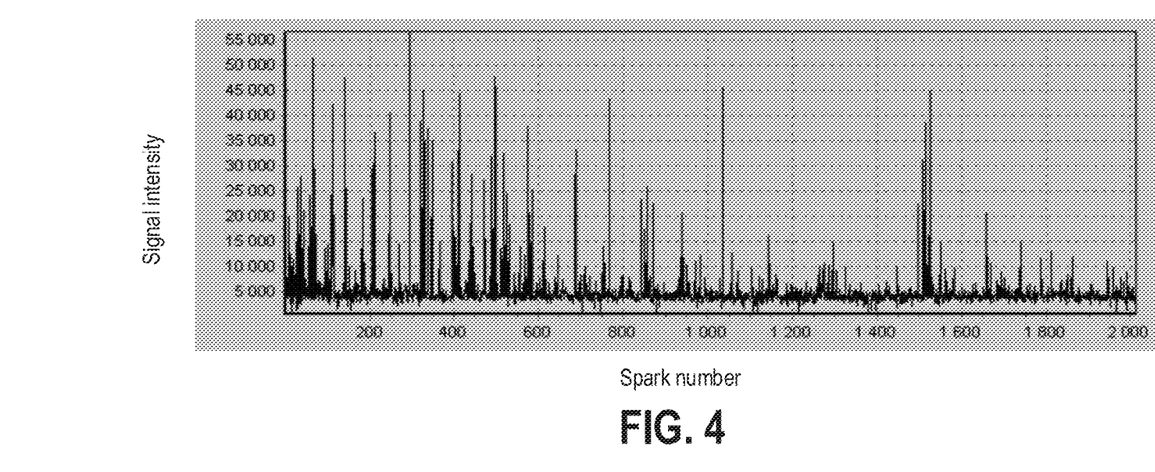
FIG. 4 shows example optical emission acquired from a channel of an optical emission spectroscopy (OES) system.
Figure 5:
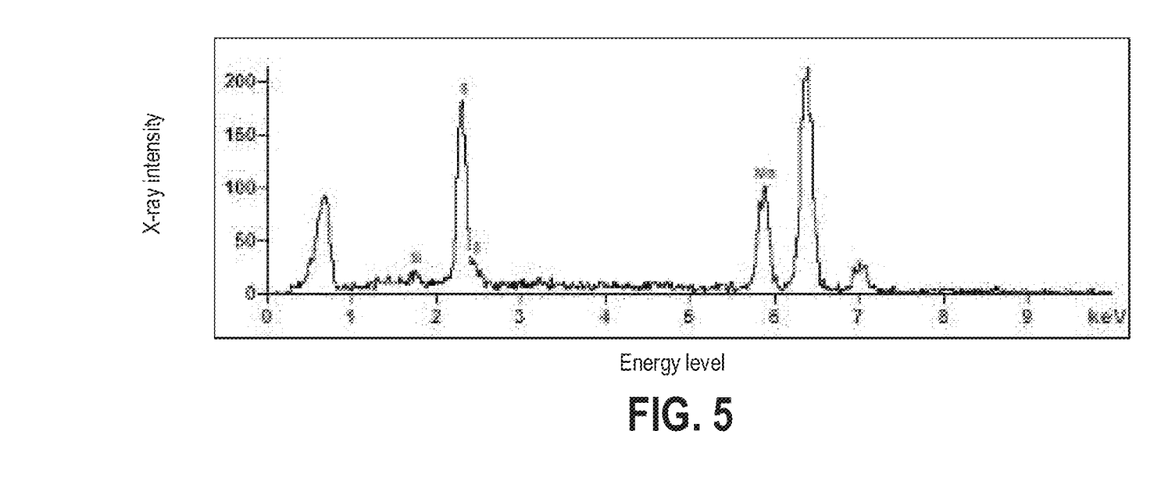
FIG. 5 shows an example X-ray intensity acquired from a detector of the CPM/EDX system.
Figure 6:
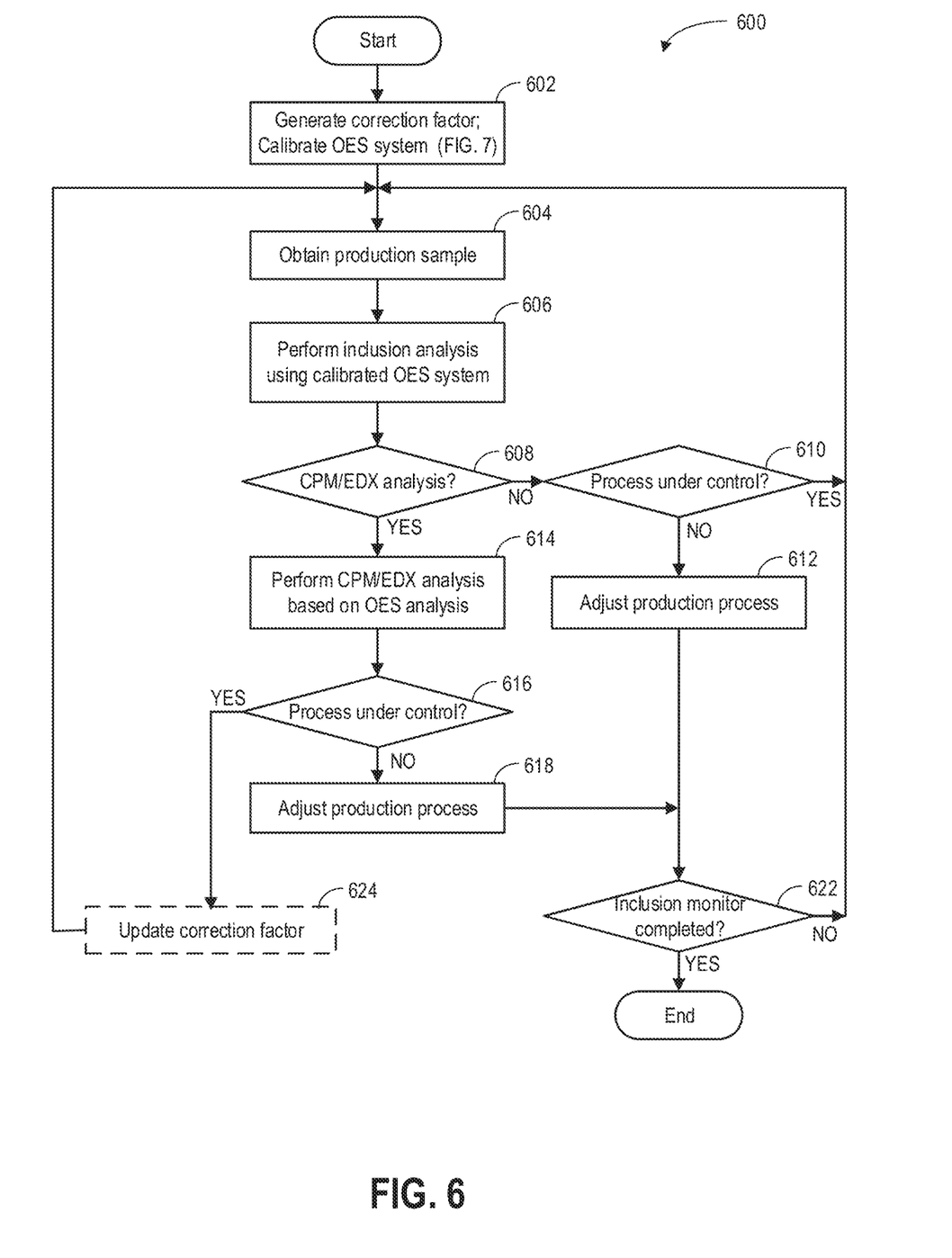
FIG. 6 is a flow chart showing an example method for analyzing sample inclusion.
Figure 7:
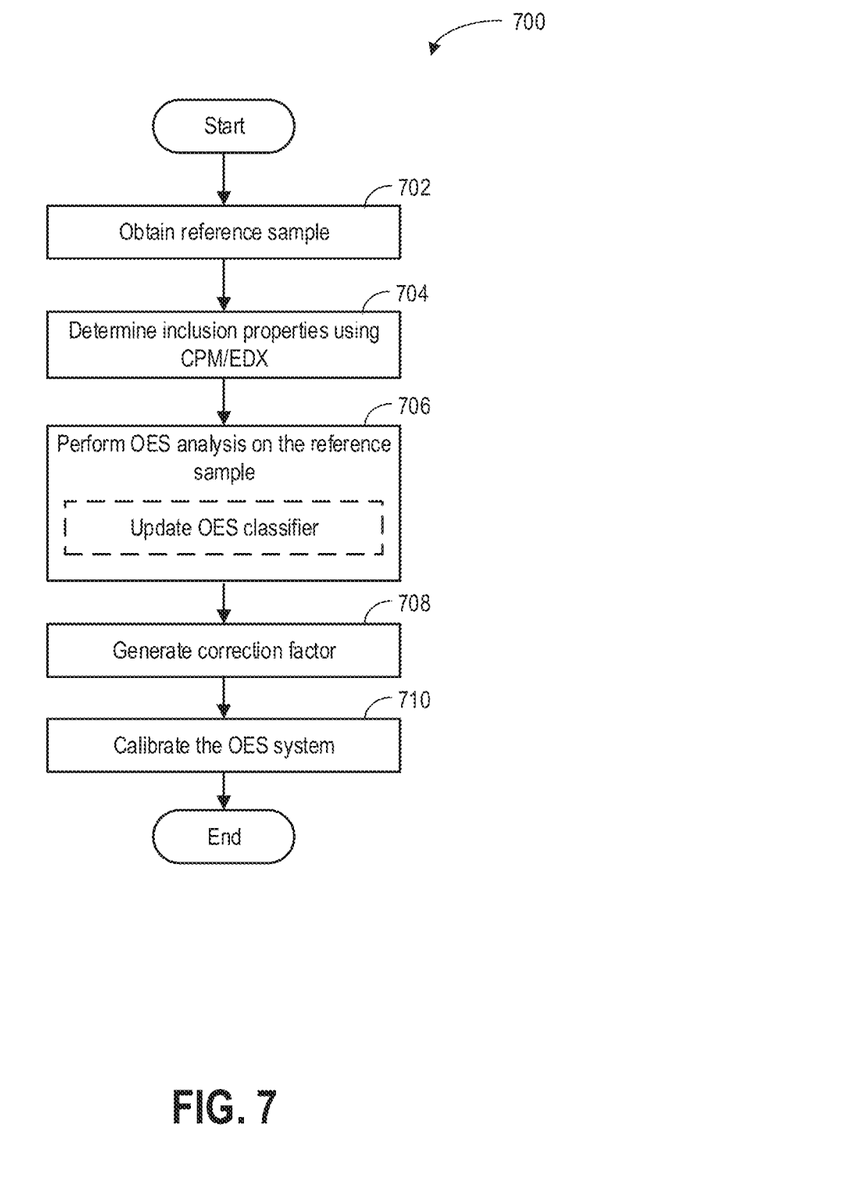
FIG. 7 shows a subroutine for calibrating the OES system.
Figure 8:
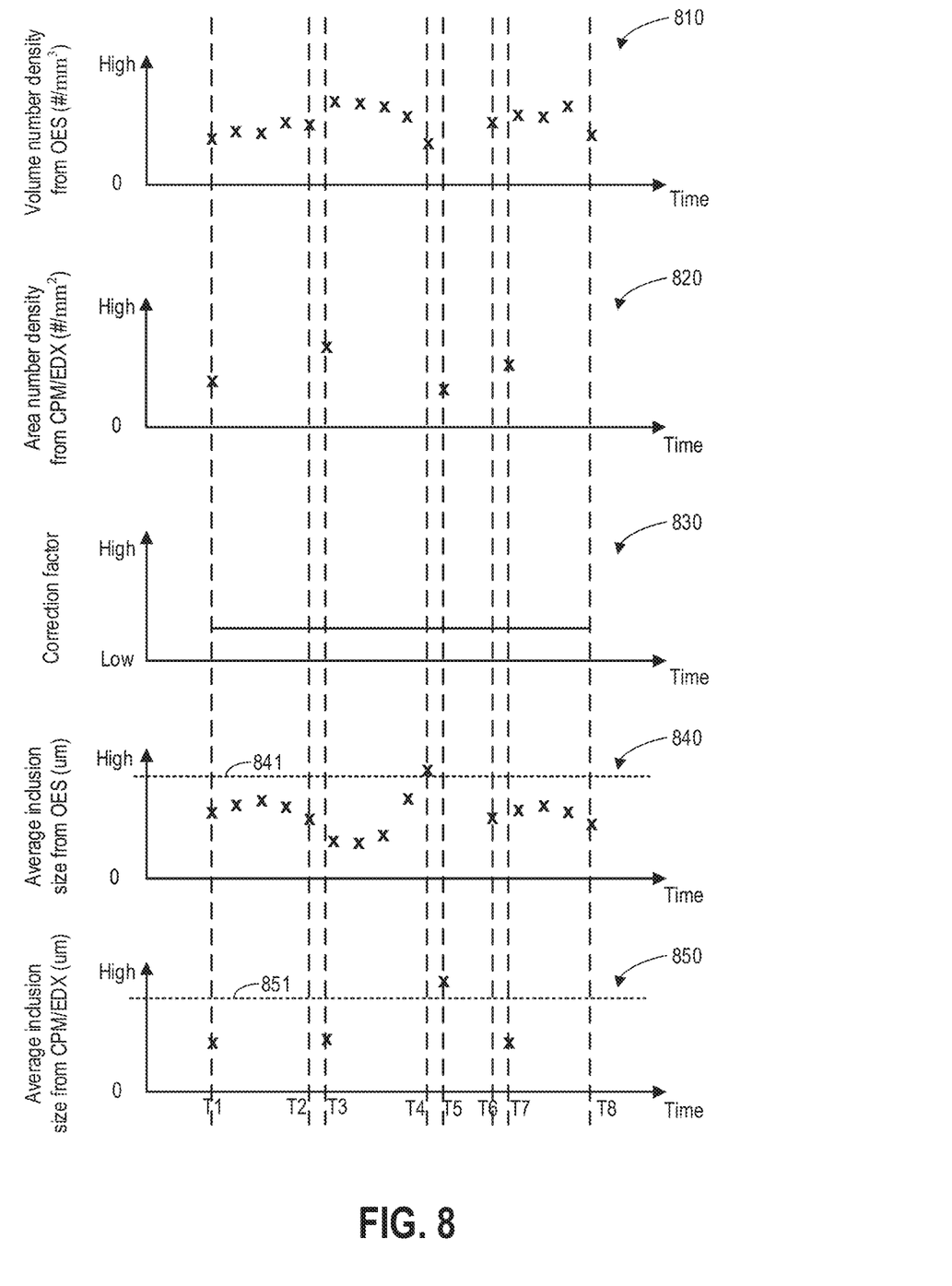
FIG. 8 shows variations of parameters and outputs of the inclusion analysis system of FIG. 2 during a production process, according to one embodiment of the invention.

In order to address the above issue, FIG. 2 shows an inclusion analysis system including an OES system and a CPM/EDX system for performing the OES analysis and CPM/EDX analysis on a sample, respectively. The OES analysis may be calibrated based on the output of the CPM/EDX analysis, and the CPM/EDX analysis may be adjusted based on the output of the OES analysis. By synergizing the two inclusion analysis methods, accurate inclusion properties may be determined timely for in-process production control. FIG. 3 is an example CPM/EDX system included in the inclusion analysis system of FIG. 2. Raw data acquired from the detectors of the OES system and the CPM/EDX systems are shown in FIG. 4 and FIG. 5, respectively. FIG. 6 shows an example method for analyzing the sample inclusions using the system of FIG. 2. After calibrating the OES system based on the OES and CPM/EDX analyses of a reference sample, as shown in FIG. 7, a production sample sampled from the production process may be analyzed by the calibrated OES system. Under certain conditions, the production sample may be selectively analyzed using the CPM/EDX system guided by the output of the OES inclusion analysis. FIG. 8 shows the changes in the parameters and outputs of the inclusion analysis system of FIG. 2 during a production process.

Turning to FIG. 1, inclusion analyses at various stages of the steel production are illustrated. As an example, liquid steel from the furnace flows to the secondary refining before being casted into slabs, billets or blooms. The slabs may further be rolled in to proper thickness. Inclusion properties of the production samples sampled at one or more production stages may be analyzed by the inclusion analysis system 200, as indicated by 102. Based on feedbacks of the inclusion analysis, one or more of the steel production process may be adjusted, as shown by dashed lines 101. For example, the production sample may be sampled after a production stage (such as furnace, secondary refining, and caster) and sent to the inclusion analysis system 200. Based on the inclusion properties reported by the inclusion analysis system 200, the corresponding production stage may be adjusted. In one embodiment, responsive to the inclusion property of the production sample obtained at a particular production stage out of a desired range, the production process upstream of the particular production stage may be adjusted. In some embodiments, one or more of the production stages upstream of the production sample sampling location may be adjusted. The inclusion properties may include one or more of inclusion type/composition, inclusion number density, size distribution, and inclusion size.

FIG. 2 shows an example inclusion analysis system 200. The inclusion analysis system 200 may include a CPM/EDX system 210 and an OES system 220. An example configuration of the CPM/EDX system is shown in detail in FIG. 3. A sample may be transferred to the CPM/EDX system 210 and/or the OES system 220 as indicated by line 211. In one embodiment, the sample may be first polished and analyzed by the CPM/EDX system 210. Then the same sample may be milled and analyzed by the OES system 220. Because the CPM/EDX analysis is nondestructive, inclusions in the same region of the sample may be analyzed by both the CPM/EDX and OES systems. In another embodiment, a first portion of the sample may be analyzed by the OES system 220, and a second portion of the sample may be analyzed by the CPM/EDX system 210.

The CPM/EDX system 210 may generate inclusion properties 212. The inclusion properties 212 may include one or more of the spatial (2D or 3D) distributions of the size, shape, and composition of the inclusion. The inclusion properties 212 may also include the inclusion area, the number density, and the average size of the inclusion. The OES system 220 may generate inclusion properties 226. The inclusion properties 226 may include one or more of the type/composition, the average size, the volume mass density, and the volume number density of the inclusion. Inclusion properties 213, a subset of inclusion properties 212, may be fed to the controller 225 of the OES system 220.

Inclusion properties 227, a subset of inclusion properties 226, may be fed to the CPM/EDX system 210.

In some embodiments, the inclusion properties 212 generated from the CPM/EDX system and the inclusion properties 226 generated from the OES system may be combined to generate an inclusion analysis report 214. The report may be generated based on the capabilities and limitations of the CPM/EDX system and the OES system to facilitate inclusion characterization. For example, the report may be generated based on the sensitivity of the CPM/EDX system and the OES system to a particular type of element. For example, comparing to the CPM/EDX system, the OES system may be more sensitive to Boron, but less sensitive to Manganese. The OES system may be advantageous in detecting small inclusions comparing to the CPM/EDX system. However, the OES system may have a theoretical upper limit for inclusions size analysis, while the CPM/EDX does not have an upper limit for inclusion size. In one embodiment, responsive to the type of element under analysis, properties of a certain type of inclusion reported in the inclusion analysis report 214 may be based on output from one of the CPM/EDX and the OES systems. For example, properties of Boron inclusions may be reported based only on the OES system output. As another example, properties of Manganese inclusions may be reported based only on the CPM/EDX system output. In another embodiment, responsive to the inclusion size, the inclusion properties may be reported based on output from one of the CPM/EDX and the OES systems. For example, if the CPM/EDX system detects that the inclusion size is under a threshold size, such as under 1 micron in diameter, the inclusion number density is reported based only on the CPM/EDX system output. In yet another embodiment, additional information about the inclusion may be extracted by comparing the outputs from the CPM/EDX system and the OES system. For example, for a sample first analyzed by SEM/EDX then OES, if the SEM/EDX reports a small inclusion area and the OES reports large inclusion volume, it may be determined that the inclusions embed deep in the sample. If the SEM/EDX reports medium inclusion area and the OES reports medium inclusion volume, it may be determined that the inclusions are mostly spherical and are cut or polished through the center.

The OES system 220 may include the electrical source 222, the optical system 223, the data acquisition unit 224, and the controller 225. In one embodiment, a small volume of the sample received by the OES system 220 may be vaporized under the electrical discharge generated between the sample and the electrical source 222. Light emitted from atoms in the vaporized sample is spatially separated by wavelength using a diffraction grating in the optical system 223. Multiple detectors (such as photomultipliers) of the optical system 223 may be positioned at different locations. Each detector receives the optical emission at a wavelength range specific to an element. The detector may record the light intensity responsive to each electrical discharge (or spark). Each wavelength range corresponds to a type of element. The signal intensity at each wavelength range corresponds to the amount of the element within the vaporized sample. For each sample, multiple locations are analyzed. The signal received by each detector may be collected and digitized by the data acquisition unit 224. As an example, FIG. 4 shows optical emission data acquired from the Aluminum wavelength range. In FIG. 4, the x-axis is the number of the spark, and the y-axis is the signal intensity. The signal intensity varies significantly across the sparks, which indicates large variation in the Aluminum amount among the vaporized volumes. The peak intensities correspond to inclusions.

The controller 225 of the OES system 220 may be configured to control the electrical source 222, optical system 223, and data acquisition unit 224 by executing computer readable instructions saved in the non-transitory memory of the controller, as shown by dashed lines 228. The controller 225 may also be configured to determine the inclusion properties by processing the digitized data from the data acquisition unit 224. For example, inclusion type/composition may be determined based on relative signal intensities from different wavelength ranges responsive to the same spark via an inclusion type classifier. The inclusion type classifier may determine inclusion type or composition by checking simultaneous occurrence of intensity peaks at different wavelength ranges. The number of inclusions may be determined based on the number of intensity peaks received responsive to sparks. The inclusion size may be estimated based on signal intensities. The volume number distribution (number per volume) may be determined based on the number of inclusions and the volume of the vaporized sample.

The controller 225 may receive one or more of the inclusion properties 213 outputted from the CPM/EDX system 210 and calibrate the data processing procedures of the controller based on the received inclusion properties 213 of the same sample. In one embodiment, the inclusion type classifier of the controller 225 may be updated based on the inclusion composition determined by the CPM/EDX system. In another embodiment, a correction factor may be generated based on the OES system output and the inclusion properties 213 determined by the CPM/EDX system. The OES system may then be calibrated by applying the correction factor to the future OES system output. In one example, the inclusion property from the CPM/EDX system may first be converted to be comparable to the inclusion property of the OES system output. The correction factor may then be calculated as the ratio between the converted inclusion property from the CPM/EDX system and the inclusion property of OES system output. The correction factor may be applied to the OES system output by multiplying the inclusion property estimated by the OES system with the correction factor. The OES system may then output or report the modified or corrected inclusion property as a part of the inclusion properties 226. In another embodiment, the correction factor may be generated based on the converted OES system output and the CPM/EDX system output.

One or more inclusion properties 227 outputted by the OES system may be sent to the CPM/EDX system to guide the scanning and data acquisition process. Inclusion properties 227 may include the average inclusion size and the inclusion type/composition. In one embodiment, the scanning step of the CPM/EDX system may be adjusted based on the average inclusion size determined by the OES system. In another embodiment, the acquisition time of the detector for detecting emitted X-rays in the CPM/EDX system may be adjusted based on the inclusion type/composition determined by the OES system.

In this way, inclusion characterization may be improved by calibrating the OES system based on outputs from the CPM/EDX system. Meanwhile, the scanning time and accuracy of the CPM/EDX system may be improved based on the inclusion information from the OES system.

In some embodiments, the OES system may be replaced by other volumetric inclusion analysis systems, such as the laser-induced breakdown spectroscopy (LIBS) system.

FIG. 3 shows an example configuration of the CPM/EDX system 210. The CPM/EDX system 210 may be a scanning electron microscopy with energy dispersive X-ray spectroscopy (SEM/EDX) system. The CPM/EDX system 210 may include a particle-optical column 315 mounted on the vacuum chamber 306. Within the particle-optical column 315, electrons generated by electron source 312 are modified by the compound lens system 314 before focused onto sample 302 by lens system 316. The incident beam 304 may scan over sample 302 by operating the scan coils 313. The sample may be held by sample stage 308.

The CPM/EDX system 210 may include multiple detectors for detecting various emissions from sample 302 in response to the irradiation of incident beam 304. A first detector 303 may detect the X-rays emitted from the sample 302. In one example, detector 303 may be a multi-channel photon-counting EDX detector. A second detector 301 may detect electrons, such as the backscattered and/or secondary electrons emitted from sample 302. In one example, detector 301 may be a segmented electron detector.

FIG. 5 shows an example X-ray energy distribution acquired with the first detector 303. The x-axis is the energy level, and the y-axis is the X-ray intensity. Different element generates X-ray at different energy level. Thus, based on energy levels of the X-ray intensity peaks, the elements of the inclusion may be determined. Based on the relative intensities of the X-ray intensity peaks, the composition of the inclusion may be further determined. The X-ray intensity and the signal to noise ratio increases by increasing the data acquisition time of the detector. The increased signal to noise ratio may improve the accuracy of inclusion characterization. However, increased data acquisition time may also increase the total scan duration.

Turning back to FIG. 3, controller 324 may control the operation of the CPM/EDX system 210. The controller may include a processor 331 and a non-transitory memory 332 for storing computer readable instructions. The controller may be configured to process the signals received from the multiple detectors, and determine the structure and the distribution of the inclusions in the sample by executing the computer readable instructions stored in the non-transitory memory 332. The controller may further be configured to operate various actuators of the CPM/EDX system by executing instructions stored in the non-transitory memory 332. For example, responsive to irradiation of the sample at a location, both electrons and X-rays emitted from the sample are acquired via the detectors. The controller then adjusts the scan coil 313 to irradiate the electron beam at another location of the sample, and subsequently acquires both the electrons and X-rays emitted from the sample. After scanning an area of the sample surface, the structure and the material composition of the scanned area may be reconstructed.

The controller 324 may adjust the parameters for scanning and signal processing responsive to inclusion properties 227 from the OES system 220. In one example, responsive to the inclusion properties 227, the controller may set the acquisition time of the detector 303 for collecting the X-ray signals, and adjust the scanning step size and dwelt time at each scanning step by adjusting the scan coils 313. The controller 324 may also receive operator inputs from the input device 328. The input device may be a mouse, a keyboard, or a touchpad.

Though a SEM/EDX system is described by way of example, it should be understood that the CPM/EDX system may be other types of charge-particle microscopy system, such as transmission electron microscopy (TEM) with EDX, scanning transmission electron microscopy (STEM) with EDX, or a dual beam tool such as a focused ion beam combined with scanning electron microscopy (FIB-SEM) with EDX. The present discussion of the SEM/EDX system is provided merely as an example of one suitable imaging modality for detecting the spatial structural and composition distribution of the inclusions in the sample.

FIG. 6 shows method 600 for analyzing sample inclusion during a production process, such as a steel production process. Inclusion properties of production sample obtained at a specific stage of the production process may be monitored using both the OES system and the CPM/EDX system. For example, all of the production samples may be analyzed using the OES system, and be selectively analyzed using the CPM/EDX system. The OES system output may be used to guide the CPM/EDX analysis to reduce the scan time and increase inclusion composition characterization accuracy. The CPM/EDX output may also be used to calibrate the OES system for improved accuracy in inclusion characterization.

Method 600 and other methods disclosed herein may be implemented by executing computer readable instructions stored in the non-transitory memories of an inclusion analysis system, such as the inclusion analysis system 200 of FIG. 2. For example, the instructions may be stored in the memories of the OES system and/or the memories of the CPM/EDX system of FIG. 2.

At 602, before analyzing a production sample, a correction factor may be generated by measuring inclusion properties of a reference sample using both the CPM/EDX system and the OES system. The OES system is then calibrated based on the correction factor. Details about the OES system calibration is shown in FIG. 7.

FIG. 7 shows a subroutine 700 for calibrating the OES system based on both the CPM/EDX analysis and the OES analysis of the reference sample.

At 702, the reference sample is obtained. In one embodiment, the reference sample may be obtained before executing method 600, before the production process. In another embodiment, the reference sample may be a production sample obtained during the production process.

At 704, the reference sample is analyzed using the CPM/EDX system. Sample properties including one or more of the inclusion compositions, the inclusion number, the area number density (number per area), and the size may be generated by the CPM/EDX system. Step 704 may include preparing (such as polishing) the sample before it is analyzed by the CPM/EDX system.

At 706, the reference sample is analyzed using the OES system. For example, the same region scanned with the CPM/EDX at 704 may be analyzed using the OES system. In some embodiment, the OES inclusion type classifier may be updated based the inclusion composition determined at 704. For example, the OES inclusion type classifier may be trained based on the inclusion composition determined by the CPM/EDX. The inclusion type/composition may then be determined using the trained inclusion type classifier. The inclusion properties determined from the OES analysis may include one or more of the inclusion types, the inclusion size and number, the volume number density, and the volume mass density. Step 706 may include modifying (such as milling, lathing, or grinding) the reference sample before it is analyzed by the OES system.

At 708, one or more of correction factors may be generated based on the inclusion properties determined using the CPM/EDX system at 704 and the inclusion properties determined using the OES system at 706. In one embodiment, a correction factor may be generated for each inclusion type. For example, the correction factor may be further adjusted to reflect the accuracy and sensitivity of each system for detecting a particular inclusion type. In another embodiment, different correction factors may be generated for different OES outputs.

In one embodiment, the correction factor may be generated to calibrate the number density output of the OES system. In one example, the inclusion area number density generated from the CPM/EDX system is $N_{mm^2}^{CPM/EDX}$ (number per mm$^2$), the inclusion volume number density generated from the OES system is $N_{mm^3}^{OES}$ (number per mm$^3$). The inclusion area number density from the CPM/EDX system $N_{mm^2}^{CPM/EDX}$ may be converted to a volume number density $N_{mm^3}^{CPM/EDX}$ so that to be comparable to the inclusion volume number density $N_{mm^3}^{CPM/EDX}$. The area number density $N_{mm^2}^{CPM/EDX}$ may be converted to volume number density $N_{mm^3}^{CPM/EDX}$ based on the volume of vaporized sample for each spark in the OES analysis, the imaging depth of the CPM/EDX analysis, and the statistical distribution of the inclusion. The statistical distribution may be determined based on the stage of the steel production at which the sample is sampled. The unitless correction factor F may then be calculated as $$F = \frac{N_{mm^3}^{CPM/EDX}}{N_{mm^3}^{OES}}.$$

In another example, the inclusion volume number density $N_{mm^3}^{OES}$ may be converted to an area density $N_{mm^2}^{OES}$. The unitless correction factor F' may then be calculated as $$F' = \frac{N_{mm^2}^{CPM/EDX}}{N_{mm^2}^{OES}}.$$

In another embodiment, a correction factor may be generated to calibrate the mass density output of the OES system. For example, the correction factor may be generated based on the ratio of a converted inclusion area mass density from the CPM/EDX analysis and the inclusion volume mass density from the OES analysis at 706. The converted inclusion area mass density from the CPM/EDX analysis may be generated by converting the area mass density from the CPM/EDX to a volume mass density. For example, the conversion may be based on the volume of vaporized sample for each spark in the OES analysis. the imaging depth of the CPM/EDX analysis, and the statistical distribution of the inclusion.

In some embodiments, the correction factor may be a number. In other embodiments, the correction factor may be in the form of a table or a function.

At 710, the OES system is calibrated with the correction factor. In one embodiment, the calibrated OES system includes the updated OES classifier determined at 706. In another embodiment, the correction factors generated at 708 are stored in the controller of the OES system. The correction factors may be applied to future OES system output. For example, after acquiring raw data from a sample different from the reference sample using the OES system, correction factor for inclusion number density may be multiplied with the inclusion volume number density determined based on the raw data to obtain the inclusion number density outputted by the calibrated OES system.

Turning back to FIG. 6, at 604, during the production process, a product sample may be obtained at a stage of the production process. For example, as shown in FIG. 1, the product sample may be taken in the liquid steel from the furnace and/or at secondary refining. The product sample may be cooled and analyzed in the solid form by the inclusion analysis system. The product sample may also be a solid steel sample obtained after casting and/or before rolling. In one embodiment, the product sample may be obtained at a predetermined frequency.

At 606, inclusion analysis may be performed on the production sample using the calibrated OES system. Inclusion properties including the type, the average size, the mass density, and the volume number density of the inclusion may be determined.

At 608, based on the inclusion properties generated by the OES system, method 600 determines whether to perform the CPM/EDX analysis on the production sample obtained at 604. In one embodiment, the CPM/EDX analysis may be performed responsive to the inclusion size generated by the OES system greater than a threshold size. The threshold size may for example be 10 μm in diameter. In another embodiment, the CPM/EDX analysis may be performed responsive to the volumetric inclusion number. For example, the CPM/EDX analysis may be performed responsive to the volumetric inclusion number less than a lower threshold number and/or higher than a high threshold number. The lower threshold number and the higher threshold number may be calculated based on extreme value metrics. In another embodiment, the CPM/EDX analysis may be performed responsive to the inclusion type determined by the OES system. For example, if the OES system detects an inclusion type not expected in the production process, the CPM/EDX analysis may be performed to further confirm the inclusion type. In another example, if the OES system detects an inclusion type (such as silicon inclusion) on which the OES system having a low detection capability, the sample may be further analyzed by the CPM/EDX system. In yet another embodiment, the CPM/EDX analysis may be performed responsive to a duration from the most recent CPM/EDX analysis. The CPM/EDX analysis may be performed at a lower frequency comparing to the OES analysis. In one example, the OES analysis may be performed on each sampled production sample, while the CPM/EDX analysis may be performed on every twenty sampled production samples. In another example, the CPM/EDX analysis may be performed after a predetermined time period. In yet another embodiment, the CPM/EDX analysis may be performed based on the trend of the OES output. The CPM/EDX analysis may be performed if the trend of a particular inclusion property is approaching a limit. For example, the trend may be determined based on the previous inclusion number of a given type (such as aluminum oxide) from the OES. If it is determined that inclusion number is approaching a limit (such as within a threshold distance from the limit), the production sample, or the next production sample, may be sent for CPM/EDX analysis. In another example, the trend may be determined based on a change rate of the inclusion property. The CPM/EDX analysis may be performed responsive to the change rate of the inclusion property exceeding a predetermined change rate limit. If it is determined to analyze the production sample using the CPM/EDX system, method 600 proceeds to 614. Otherwise, method 600 proceeds to 610. In yet another embodiment, the CPM/EDX analysis may be performed if the calibration flag is set.

At 610, based on the OES system output at 606, method 600 determines whether the production process is under control. In one example, the process may be determined to be under control if the inclusion properties are within a desired range. In another example, the process may be determined to be under control if the trend (such as the change rate) of the inclusion property is within a predetermined change rate limit. If the process is under control, another production sample is obtained at 604. If the process is not under control, the production process is adjusted at 612.

At 612, the production process is adjusted based on the inclusion properties determined by the OES system at 606. For example, responsive to high oxygen content detected from the OES analysis, Aluminum may be added to the steel for deoxidization. In another example, responsive to the Al/Ca ratio out of the desired Al/Ca range, the amount of Calcium added to the steel may be adjusted during the steel production process. In another example, responsive to the Al/Ca ratio out of the desired Al/Ca range, the amount of Aluminum and/or Calcium added to the steel may be adjusted during the steel production process. In another example, the production process may be adjusted based on the trend of the OES system output.

At 614, the production sample obtained at 604 is analyzed using the CPM/EDX analysis guided by the output of the OES inclusion analysis at 606. The inclusion properties determined from the CPM/EDX analysis may include spatial distribution of the size, number, and type of the inclusion. The inclusion properties determined from the CPM/EDX analysis may further include the area number density and mass density of the inclusion. In some embodiments, a combined inclusion property report may be generated based on the CPM/EDX analysis and the OES analysis at 606.

In one embodiment, the scanning step size of the CPM/EDX system may be adjusted based on the inclusion size determined by the OES system. In one example, the scanning step size may increase with increased inclusion size determined by the OES system. In another example, the CPM/EDX scan may be performed with varied scanning steps. The sample may be scanned at a first scanning step size if no inclusion is detected. The first scanning step increases with increased inclusion size determined by the OES system. Upon detecting an inclusion, the CPM/EDX may be performed at a second scanning step size smaller than the first scanning step size. The second scanning step size may be predetermined. By adjusting the scanning step size based on the predicted inclusion size from the OES system, the CPM/EDX analysis duration may be reduced.

In another embodiment, the acquisition time for the X-ray detector in the CPM/EDX system may be adjusted based on the element type predicted by the OES system at 606. In one example, if the CPM/EDX system has low sensitivity to the predicted element by the OES system, the acquisition time of the X-ray detector may be increased. For example, the detector acquisition time may be increased if the OES system predicts the inclusion includes Boron or Manganese. In another example, if the CPM/EDX system has high sensitivity to the predicted element by the OES system, the acquisition time of the X-ray detector may be decreased to reduce the total scan duration.

At 616, based on the inclusion properties determined at 614, method 600 determines whether the production process is under control. In one example, the process may be determined to be under control if the inclusion properties are within a desired range. If the process is under control, method 600 proceeds to 624. If the process is not under control, the production process is adjusted at 618.

At 618, the production process is adjusted based on the inclusion properties determined at 614. In one embodiment, production process may be adjusted based on the trend or variation of the inclusion properties in a given time period. The trend (such as increase or decrease in number) may be determined based on multiple previous CPM/EDX inclusion outputs. For example, responsive to increasing oxygen content, Aluminum may be added to the steel for deoxidization. In another example, responsive to the Al/Ca ratio approaching the upper or lower limit of the desired Al/Ca range, the amount of Calcium added to the steel may be adjusted during the steel production process. In another example, responsive to the Al/Ca ratio approaching the upper or lower limit of the desired Al/Ca range, the amount of Aluminum and/or Calcium added to the steel may be adjusted during the steel production process.

In other embodiments, the OES system may be calibrated only once at 602, and no further re-calibration is conducted. For example, the calibration flag may be set as always zero to avoid re-calibration.

At 622, the status of the inclusion monitoring process is checked. If the inclusion monitoring process ends, method 600 exits. Otherwise, another production sample is obtained at 604.

At 624, the correction factor may be optionally updated based on the outputs of the OES analysis at 606 and the CPM/EDX analysis at 614. In some embodiments, the correction factors may be updated responsive to CPM/EDX analysis. For example, the correction factors may be updated based on inclusion properties from CPM/EDX analysis which cannot be monitored by the OES analysis. Similar to step 708 of FIG. 7, the correction factors may be recalculated based on the inclusion properties of the same production sample generated by both systems. For example, the correction factor may be recalculated based on the inclusion volume number density generated with OES analysis at 606 and the inclusion area number density generated with CPM/EDX analysis at 614. As another example, the correction factor may be recalculated based on the inclusion volume mass density generated with OES analysis at 606 and the inclusion area mass density generated with CPM/EDX analysis at 614. The updated correction factor may be stored in the controller of the OES system and applied to future OES analysis.

In this way, the production process may be adjusted in-process based on the inclusion properties of the production samples determined using the OES analysis. The CPM/EDX analysis may be selectively performed on the production samples. Responsive to both the OES analysis and the CPM/EDX analysis being performed on one production sample, the OES system may be calibrated based on the outputs of the OES and CPM/EDX analyses. Further, the CPM/EDX analysis is performed based on the OES analysis output to reduce scan time and improve composition characterization.

FIG. 8 are timelines showing variations of parameters and outputs of the inclusion analysis system of FIG. 2. The parameters and outputs may relate to one type of inclusion. The x-axes are time. The time increases as indicated by the arrows of the x-axes. Plot 810 shows the volume number density reported by the OES system. The volume number density increases as indicated by the arrow of the y-axis. Plot 820 shows the area number density reported by the CPM/EDX system. The area number density increases as indicated by the arrow of the y-axis. Plot 830 shows the unitless correction factor. The value of the correction factor increases as indicated by the arrow of the y-axis. Plot 840 shows the average inclusion size reported by the OES system. The average inclusion size may be estimated based on the volume number density and the average mass reported by the OES system. The average inclusion size increases as indicated by the arrow of the y-axis. Plot 850 shows the average inclusion size reported by the CPM/EDX system. The average inclusion size may be estimated based on the area number density and the mass density reported by the CPM/EDX system. The average inclusion size increases as indicated by the arrow of the y-axis.

At T1, the correction factor (plot 830) is calculated based on the volume number density from OES system (plot 810) and the area number density from the CPM/EDX system (plot 820) of a reference sample. The correction factor may be calculated according to the method of FIG. 7. For example, the correction factor may be a ratio between the converted area number density from the CPM/EDX system and the volume number density from the OES system. In another example, the correction factor may be a correction function. The OES system and the CPM/EDX system may also output the average inclusion sizes (plots 840 and 850).

From T1 to T2, the production samples are sampled at a stage of the production process and analyzed using the OES system calibrated with the correction factor. The correction factor 803 remains at the same value from T1 to T2. In one example, the production samples are sampled at a predetermined frequency. As a result, the volume number density and the average inclusion size are reported periodically by the OES system in plots 810 and 840, respectively.

At T2, the production sample analyzed by the OES system is sent to the CPM/EDX system for inclusion analysis. The duration between T1 and T2 may be predetermined. In other words, the production sample may be periodically analyzed by both the OES and CPM/EDX systems. The CPM/EDX system may analyze the sample at a lower frequency than the OES system. After a delay, at T3, the CPM/EDX system outputs the area number density and the average inclusion size of the inclusion.

From T3 to T4, the production sample is obtained regularly and analyzed by the recalibrated OES system only. The volume number density and average size of the inclusion are estimated by the OES system, as shown in plots 810 and 840.

At T4, responsive to the average inclusion size determined by the OES system (in plot 840) higher than a threshold size 841, the same production sample is sent to be analyzed using the CPM/EDX system.

At T5, responsive to the CPM/EDX system confirming the average inclusion size higher than a threshold size 851, the production process is adjusted. The threshold size 841 may be the same as the threshold size 851. Adjusting the production process may include adding or removing materials upstream to the stage that the production is sampled.

At T6, the production sample is obtained and analyzed by the OES system. The same production sample is analyzed by the CPM/EDX system, and the CPM/EDX system outputs the area number density and the average inclusion size at T7. Based on the volume number density in plot 810 at T6 and the area number density in plot 820 at T7, based on the correction factor 830.

From T7 to T8, inclusions in the production sample may be monitored at a predetermined frequency by the OES system.

In this way, the sample inclusion property is continuously monitored during the production process using the inclusion analysis system including an OES system and a CPM/EDX system. Because the OES system has a shorter analysis duration comparing to the CPM/EDX system, each production sample sampled from a certain production stage may be analyzed by the OES system. The production samples may be selectively analyzed using the CPM/EDX system. The OES system outputs may guide the CPM/EDX analysis. As such, the production process may be adjusted in real-time based on feedback from the inclusion properties determined by the inclusion analysis system.

The technical effect of calibrating the OES system based on the CPM/EDX analysis and the OES analysis of a sample is to improve the accuracy of the inclusion characterization by the OES system. The technical effect of adjusting the CPM/EDX analysis based on the OES system output is that the scanning time for CPM/EDX analysis may be reduced, and the composition of the inclusion may be detected more accurately. The technical effect of analyzing the production sample using the OES system at a higher frequency is that the production process may be adjusted in real time. The technical effect of selectively analyzing the production sample using the CPM/EDX system at a lower frequency is to confirm the output from the OES system.

In one presentation, a method for analyzing sample inclusions comprises generating a first set of inclusion properties of a sample using an optical emission spectrometry (OES) system; updating a charged-particle microscopy with energy dispersive X-ray spectroscopy (CPM/EDX) system based on the first set of inclusion properties; and generating a second set of inclusion properties of the sample using the updated CPM/EDX system.

In one embodiment, a method for analyzing sample inclusions comprises generating a correction factor based on inclusion properties of a first sample determined using both an optical emission spectrometry (OES) system and a charged-particle microscopy with energy dispersive X-ray spectroscopy (CPM/EDX) system, and determining an inclusion property of a second, different, sample using the OES system calibrated with the correction factor. In a first example of the method, the method further includes wherein generating the correction factor based on inclusion properties of the first sample using both the OES system and the CPM/EDX system includes generating the correction factor based on an inclusion volume number density determined using the OES system and an inclusion area number density determined using the CPM/EDX system. A second example of the method optionally includes the first example and further includes wherein generating the correction factor based on the inclusion volume number density determined using the OES system and the inclusion area number density determined using CPM/EDX system includes converting the inclusion area number density determined using the CPM/EDX system to a second inclusion volume number density, and generating the correction factor based on the second inclusion volume number density and the inclusion volume number density determined using the CPM/EDX system. A third example of the method optionally includes one or more of the first and second examples, and further includes wherein determining the inclusion property of the second sample using the OES system calibrated with the correction factor includes determining an inclusion volume number density of the second sample using the OES system calibrated by the correction factor. A fourth example of the method optionally includes one or more of the first to third examples, and further includes wherein calibrating the OES system with the correction function includes multiplying an inclusion volume number density output of the OES system with the correction factor. A fifth example of the method optionally includes one or more of the first to fourth examples, and further includes wherein the inclusion property of the second sample is not determined using the CPM/EDX system. A sixth example of the method optionally includes one or more of the first to fifth examples, and further includes updating an inclusion type classifier of the OES system based on an inclusion composition of the first sample determined using the CPM/EDX system. A seventh example of the method optionally includes one or more of the first to sixth examples, and further includes wherein calibrating the OES system with the correction factor includes calibrating an inclusion mass density output of the OES system based on the correction factor. An eighth example of the method optionally includes one or more of the first to seventh examples, and further includes obtaining the first sample at a stage of production process at a first time point, obtaining the second sample at the stage of production process at a second, later, time point, and adjusting the production process based on the inclusion property of the second sample. A ninth example of the method optionally includes one or more of the first to eighth examples, and further includes, wherein the first sample is a reference sample, and the method further comprising obtaining the second sample at a stage of production process, and adjusting the production process based on the inclusion property of the second sample.

In one embodiment, a method for analyzing sample inclusions comprises generating a first set of inclusion properties of a first sample using an optical emission spectrometry (OES) system; updating a charged-particle microscopy with energy dispersive X-ray spectroscopy (CPM/EDX) system based on the first set of inclusion properties; generating a second set of inclusion properties of the first sample using the updated CPM/EDX system; generating a correction factor based on the first set inclusion properties and the second set of inclusion properties; calibrating the OES system with the correction factor; and analyzing a second, different, sample using the calibrated OES system. In a first example of the method, the method further includes wherein the first set of inclusion properties includes an inclusion size, and updating the CPM/EDX system based on the first set of inclusion properties includes adjusting a scanning step of the CPM/EDX system based on the inclusion size. A second example of the method optionally includes the first example and further includes, wherein the first set of inclusion properties includes an inclusion type, and updating the CPM/EDX system based on the first set of inclusion properties includes adjusting an acquisition time of a detector of the CPM/EDX system based on the inclusion type. A third example of the method optionally includes one or more of the first and second examples, and further includes, wherein the first set inclusion properties includes an inclusion volume number density and the second set inclusion properties includes an inclusion area number density, and generating the correction factor based on the first set inclusion properties and the second set of inclusion properties includes generating the correction factor based on both the inclusion volume number density and the inclusion area number density.

In one embodiment, a system for analyzing sample inclusions includes: an optical emission spectrometry (OES) system; a charged-particle microscopy with energy dispersive X-ray spectroscopy (CPM/EDX) system; and a controller with computer readable instructions stored on a non-transitory memory configured to: generate a correction factor based on inclusion properties of a first sample determined using both the OES system and the CPM/EDX system; calibrate the OES system based on the correction factor; and determine inclusion properties of a second, different, sample using the calibrated OES system. In a first example of the system, the method further includes, wherein the controller is further configured to determine inclusion properties of the second sample by analyzing the second sample using the CPM/EDX system responsive to the inclusion properties of the second sample determined using the calibrated OES system. A second example of the system includes the first example, and further includes, wherein the second sample is analyzed using the CPM/EDX system responsive to an inclusion size of the second sample determined using the calibrated OES system. A third example of the system optionally includes the first to second examples, and further includes, wherein the second sample is analyzed using the CPM/EDX system responsive to an inclusion type of the second sample determined using the calibrated OES system. A fourth example of the system optionally includes the first to third examples, and further includes, wherein the second sample is analyzed using the CPM/EDX system responsive to an inclusion number or an inclusion density of the second sample determined using the calibrated OES system. A fifth example of the system optionally includes the first to fourth examples, and further includes, wherein the second sample is analyzed using the CPM/EDX system responsive to a duration from a previous inclusion analysis using the CPM/EDX system.

The invention claimed is:

1. A method for analyzing sample inclusions, comprising;
    calibrating an optical emission spectrometry (OES) system using a calibration factor, wherein the calibration factor is generated based on inclusion properties of a first sample determined using both the OES system and a charged-particle microscopy with energy dispersive X-ray spectroscopy (CPM/EDX) system; and
    determining, with the calibrated OES system, an inclusion property of a second, different sample.

2. The method of claim 1, wherein generating the correction factor based on inclusion properties of the first sample determined using both the OES system and the CPM/EDX system includes generating the correction factor based on an inclusion volume number density determined using the OES system and an inclusion area number density determined using the CPM/EDX system.

3. The method of claim 2, wherein generating the correction factor based on the inclusion volume number density determined using the OES system and the inclusion area number density determined using CPM/EDX system includes converting the inclusion area number density determined using the CPM/EDX system to a second inclusion volume number density, and generating the correction factor based on the second inclusion volume number density and the inclusion volume number density determined using the CPM/EDX system.

4. The method of claim 2, wherein determining the inclusion property of the second sample using the calibrated OES system includes determining an inclusion volume number density of the second sample using the calibrated OES system.

5. The method of claim 2, wherein calibrating the OES system using the correction factor includes multiplying an inclusion volume number density output of the OES system with the correction factor.

6. The method of claim 1, wherein the inclusion property of the second sample is not determined using the CPM/EDX system.

7. The method of claim 1, further comprising updating an inclusion type classifier of the OES system based on an inclusion composition of the first sample determined using the CPM/EDX system.

8. The method of claim 1, wherein calibrating the OES system with the correction factor includes calibrating an inclusion mass density output of the OES system based on the correction factor.

9. The method of claim 1, further comprising obtaining the first sample at a stage of production process at a first time point, obtaining the second sample at the stage of production process at a second, later, time point, and adjusting the production process based on the inclusion property of the second sample.

10. The method of claim 1, wherein the first sample is a reference sample, and the method further comprising obtaining the second sample at a stage of production process, and adjusting the production process based on the inclusion property of the second sample.

11. A charged-particle microscope, comprising:
    a detector for acquiring energy dispersive X-ray spectroscopy (EDX) data, and
    a controller with computer readable instructions stored on a non-transitory memory, by executing the computer readable instructions, the charged-particle microscope is configured to:
    receive inclusion properties of a first sample determined using an OES system;
    acquire EDX data of the first sample via the detector;
    determine inclusion properties of the first sample based on the EDX data;
    generate a correction factor based on both the received inclusion properties from the OES system and the determined inclusion properties based on the EDX data; and
    output the correction factor to the OES system for calibrating the OES system.

12. The charged-particle microscope of claim 11, wherein the charged-particle microscope is further configured to: update the charged-particle microscope based on the received inclusion properties determined using the OES system.

13. The charged-particle microscope of claim 11, wherein the received inclusion properties include an inclusion size.

14. The charged-particle microscope of claim 11, wherein the received inclusion properties include an inclusion type.

15. The charged-particle microscope of claim 11, wherein the received inclusion properties include an inclusion volume number density, and the determined inclusion properties of the first sample based on the EDX data include an inclusion area number density, and generating the correction factor includes generating the correction factor based on both the inclusion volume number density and the inclusion area number density.

16. An OES system, comprising:
    a controller with computer readable instructions stored on a non-transitory memory, wherein by executing the computer readable instructions, the OES system is configured to:
    determine inclusion properties of a first sample;
    receive inclusion properties of the first sample determined using a CPM/EDX system;
    generate a correction factor based on both of the measured inclusion properties and the received inclusion properties of the first sample;
    calibrate the OES system based on the correction factor; and determine inclusion properties of a second sample with the calibrated OES system.

\* \* \* \* \*